United States Patent [19]

Kranz

[11] Patent Number: 5,015,817
[45] Date of Patent: May 14, 1991

[54] METHOD FOR PRODUCING A HOLLOW SHAFT ENDOPROSTHESIS

[75] Inventor: Curt Kranz, Berlin, Fed. Rep. of Germany

[73] Assignee: Johnson & Johnson, New Brunswick, N.J.

[21] Appl. No.: 452,735

[22] Filed: Dec. 21, 1989

[30] Foreign Application Priority Data

Dec. 23, 1988 [DE] Fed. Rep. of Germany ....... 3844155

[51] Int. Cl.$^5$ .............................................. B23K 15/00
[52] U.S. Cl. ........................... 219/121.14; 219/121.64; 623/22; 623/23
[58] Field of Search ...................... 219/121.13, 121.14, 219/121.64; 623/22, 23

[56] References Cited

U.S. PATENT DOCUMENTS

| 4,608,052 | 8/1986 | Van Kampen et al. | ............... 623/22 |
| 4,673,409 | 6/1987 | Van Kampen | .................. 623/22 X |
| 4,687,675 | 8/1987 | Nakano et al. | . |
| 4,718,914 | 1/1988 | Frey et al. | .............................. 623/23 |
| 4,752,295 | 6/1988 | Frey et al. | ......................... 623/23 X |

FOREIGN PATENT DOCUMENTS

| 0289922 | 11/1988 | European Pat. Off. . |
| 837294 | 4/1952 | Fed. Rep. of Germany . |
| 2824118 | 7/1980 | Fed. Rep. of Germany . |
| 3342562 | 6/1985 | Fed. Rep. of Germany . |
| 3711426 | 10/1988 | Fed. Rep. of Germany . |
| 3716026 | 12/1988 | Fed. Rep. of Germany . |

Primary Examiner—C. L. Albritton
Attorney, Agent, or Firm—Spencer & Frank

[57] ABSTRACT

Method for producing a hollow shaft endoprosthesis, in particular a hip joint prosthesis, comprising the following stages:
  Producing two half-tubings, which may be connected together to form the shape of the shaft of the prosthesis, whereby they touch in the region of two welding seams substantially running in a longitudinal direction, by moulding or forging,
  welding together both moulded or forged half-tubings in the region of the welding seams.

20 Claims, 1 Drawing Sheet

METHOD FOR PRODUCING A HOLLOW SHAFT ENDOPROSTHESIS

CROSS REFERENCE TO RELATED APPLICATION

This application claims the priority of the Federal Republic of Germany application No. P 38 44 155.1 filed Dec. 23rd, 1988, which is incorporated herein by reference.

BACKGROUND OF THE INVENTION

The present invention relates to a method for producing a hollow shaft endoprosthesis, in particular a hip joint prosthesis.

Hollow shaft endoprostheses have until now, usually been cast-moulded out of metal alloys. This processing method can only be used for a certain number of materials. The most widely used cast-mouldable materials for making prostheses shafts are a cobalt-chrome-molybdenum cast alloy and 316-cast steel. A disadvantage is that these materials have a low resistance to fatigue, so that fatigue fractures can occur due to large bending stress fluctuations. Other materials, such as the chrome-nickel-molybedenum-titanium wrought alloy, the cobalt-chrome-nickel-molybedenum-titanium wrought alloy and the titan-aluminum-vanadium wrought alloy were only used to produce solid prostheses in the past. It is not economical to produce hollow shafts by machining a solid bit.

SUMMARY OF THE INVENTION

It is an object of the invention to provide a method for producing a hollow shaft endoprosthesis of the above-mentioned type, in which the shape of the hollow shaft prosthesis can be easily modified, in particular with regard to the shape and structure of the inner and outer wall surface areas.

The above and other objects are accomplished according to the invention by the provision of a method comprising the following stages:

Producing two half tubings, which may be connected together to form the shape of the shaft of the prosthesis, whereby they touch in the region of two welding seams substantially running in a longitudinal direction, by moulding or forging, welding together both moulded or forged half-tubings in the region of the welding seams.

The invention is based on the realization that the preferred, titanium-aluminum-vanadium wrought alloy to be used can be shaped into any desired base parts by known methods such as moulding or forging, and that these base parts can be connected together by welding. A distinct advantage is the uncomplicated and easy workability of the base parts prior to welding, as this is far easier than the finishing work that has to be carried out on a moulded hollow shaft or the utilisation of a complicated mould-core.

It was found that the titanium-aluminum-vanadium wrought alloy is a very good material for constructing prostheses due to its good biocompatibility, high resistance to fatigue and good corrosion-resistance. This material can be worked economically by forging and mould and weld methods since only simple parts are required and the production time per piece is low.

The base parts are semi-tubular in shape. These semi-tubular parts are, if possible, already moulded or forged with a diminishing thickness from the end of the shaft near the joint to the end of the shaft far away from the joint. The base part can be finished, preferably by chemical abrasion, in order to obtain a thickness smaller than the minimum achievable forging thickness.

The shaft wall can be intentionally weakened in part, in order to locally vary the bending and longitudinal rigidity of the shaft.

Openings in the walls of the semi-tubular parts can be formed during moulding or forging. Because of the two-stage production process possible burrs can be removed quickly and unproblematically prior to the two parts being joined together.

Similarly, other deviations from a regular form, such as, for example, recesses in the concave and convex surfaces of the semi-tubular parts, can at least be preformed during moulding or forging.

The two parts are connected together, as described in a preferred embodiment of the invention, by electron beam welding. This welding method is characterized by very narrow and uniform welding seams and is therefore of a quality high enough to meet the set requirements for prostheses shafts. In addition, the areas on either side of the welding seam affected by warmth radiation are much narrower than those areas affected by WIG-welding (Wolfram inert gas). Furthermore, electron beam welding requires less finishing work to be carried out on the welding seam.

If the connected hollow shaft has openings it can be filled with polyethylene. This measure is necessary, as openings could lead to bone material growing into the hollow area of the shaft and this is a hindrome when having to, in some cases, remove the prosthesis.

The low rigidity of polyethylene does not greatly influence the optimal shape and material characteristics of the hollow prosthesis. The openings are coated with apatite in order to prevent the bone from coming in direct contact with polyethylene at the openings.

It is advantageous to fill the recesses with a Porocoat material if these are on the convex outer surface of the prosthesis shaft.

The neck part of the preferred embodiment of the prosthesis consists of a cone attachment onto which ball joints of varying diameters and cone lengths can be attached.

DESCRIPTION OF THE PREFERRED EMBODIMENT

Figure 1:
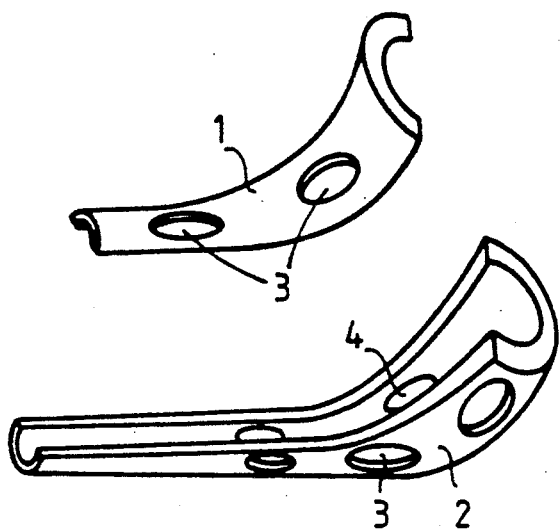
FIG. 1 is a perspective view of two moulded or forged half-tubings which have been produced using the method according to the invention.

In the first stage of the production method two differing half-tubings 1 and 2, as illustrated in FIG. 1, are moulded or forged. The half-tubings 1 and 2 are shaped to fit together. The preferred material to be used is a titanium-aluminum-vanadium wrought alloy. This material cannot be cast-moulded but possesses many characteristics favorable for arthroplastics.

The two half-tubings 1 and 2 are shaped in such a way that they can be connected together to form a curved tube with a continually increasing diameter and a continually increasing wall thickness in one common direction. The continual variation of the wall thickness in the axial direction of the shaft and the insertion of certain openings 3 or recesses 4 in the inner surface of both half-tubings have already been produced during moulding or forging. Such constructive detail enables the stress distribution in the prosthesis to approximately vary according to the physiological rigidity and the bending properties of the surrounding bone.

The half-tubings 1 and 2 are the medial, outward curving part (half-tubing 1) and the lateral, inward curving part (half-tubing 2) of the hollow shaft. This division is technologically advantageous since the outward curving part is shorter than the inward curving part at the end of the shaft far away from the joint. (Hereby the simultaneously filed patent application one is referred to 07/452,739, entitled "ENDOPROSTHESIS", the same inventor.)

Both semi-tubings 1 and 2 are deburred and planed after forging and moulding and, if required, after the insertion of openings and/or recesses. A possible finishing, by chemical milling or any other cutting method, to better the continual decreasing wall thickness on the inside or on the outside is unproblematic in this "cut-open" state.

Figure 2:
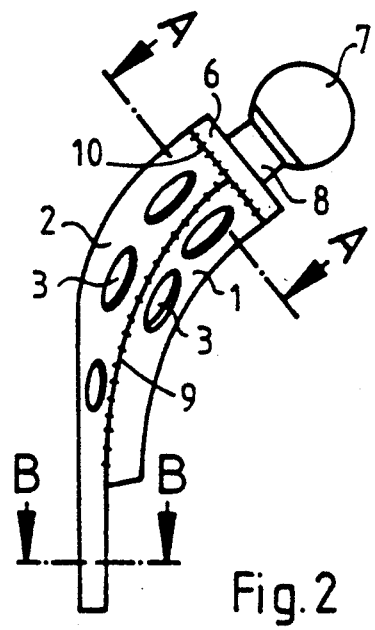
FIG. 2 is a side elevation of a welded hollow shaft produced according to the invention.
Figure 3:
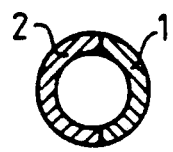
FIG. 3 is a sectional view A—A of the welded hollow shaft according to FIG. 2.
Figure 4:
FIG. 4 is a sectional view B—B of the welded hollow shaft according to FIG. 2.

As shown in FIG. 2, semi-tubings 1 and 2 can be welded together, as shown by welding seam 9. Also, a joint part 6 can be welded at a joint end, as shown by welding seam 10. High quality welding, such as electron beam welding can be used.

Recesses in the outer wall surface of the hollow shaft 5 are filled up with Porocoat material, since it is easier to break away bone material from the surface than it is to break away a bone spar from the inside of the prosthesis.

Figure 5:
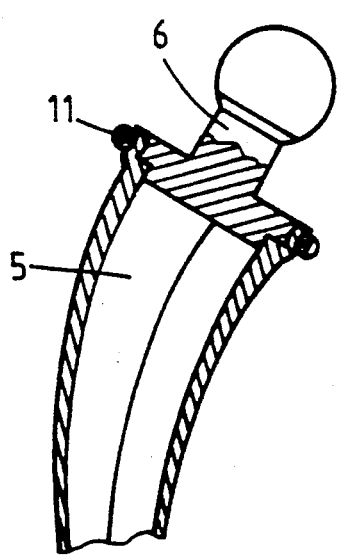
FIG. 5 is a partially sectional elevational view of a hollow shaft prosthesis with a detachable head part.

A further variation, by which the explantation of a prosthesis is made possible, is illustrated in FIG. 5. A joint part 6 can include a joint, such as an element 7 disposed on a connecting member 8. The joint part 6 is not welded to the hollow shaft but is detachably flanged to it. This can preferably be done with a bracing ring 11 with a predetermined breaking point. The inside of the hollow shaft is therefore easily accessible after breaking off the joint part 6. The surgeon can then remove any of the bone that may have grown into the hollow area of the shaft, using a burr or a drilling machine, without damaging the cortical. It will be understood that the above description of the present invention is susceptible to various modifications, changes and adaptations, and the same are intended to be comprehended within the meaning and range of equivalents of the appended claims.

What is claimed is:

1. Method for producing a hollow shaft endoprosthesis, in particular a hip joint prosthesis, comprising the following steps:
   Producing two half-tubings, which may be connected together to form the shape of the shaft of the prosthesis, whereby said half-tubings touch in the region of two welding seams substantially running in a longitudinal direction, by one of moulding and forging, and
   welding together both said half-tubings in the region of said welding seams.

2. Method as defined in claim 1, wherein the said half-tubings consist of a titanium-aluminum-vanadium (TiA16V4) wrought alloy.

3. Method as defined in claim 1, wherein said half-tubings have a joint end and an end away from said joint end, and a continually diminishing thickness of the said half-tubings from the joint end to the end away from the joint end is refined and finished.

4. Method as defined in claim 1, wherein said producing step includes forming openings in an outer side of said half-tubings.

5. Method as defined in claim 4, wherein said openings on the outer side of said shaft are covered over, a shaft opening far away from the joint end is plugged, the hollow area of said shaft is filled with polyethylene, the coverings and the plug are removed and the surface of the polyethylene is covered with apatite in the region of said openings.

6. Method as defined in claim 1, wherein said producing step includes forming said half-tubings with convex outer surfaces, and recesses are formed convex outer surfaces of said half-tubing and filled with Porocoat material.

7. Method as defined in claim 1, wherein said producing step includes said half-tubings with concave inner surfaces, and recesses are formed in the concave inner surfaces of said half-tubings.

8. Method as defined in claim 1, wherein said half-tubings have a joint end and an end away from said joint end, and an attachment cone is welded onto the joint end of said hollow shaft.

9. Method as defined in claim 1, wherein said half-tubings have a joint end and an end away from said joint end, and an attachment cone is detachably connected to the joint end of said hollow shaft by means of a bracing ring with a predetermined breaking point.

10. Method as defined in claim 1, wherein said half-tubings are welded together by electron beam welding.

11. Method as defined in claim 8, wherein said welding seams between said two half-tubings and said welding seam between said attachment cone and the joint end of said hollow shaft are planned by one of manual planing and a planing device.

12. Method as defined in claim 8, wherein said welding seams between said two half-tubings are planned by one of manual planing and a planing device.

13. Method as defined in claim 8, wherein said welding seam between said attachment cone and the joint end of said hollow shaft is planed.

14. Method as defined in claim 1, wherein said half-tubings have a joint end and an end away from said joint end, and a continually diminishing thickness of the said half-tubings from the joint end to the end away from the joint end is produced by chemical milling.

15. Method as defined in claim 1, wherein said producing step includes forming openings in an outer side of said half-tubings, and said openings are deburred and planed.

16. Method as defined in claim 15, wherein said openings on the outer side of said shaft are covered over, a shaft opening far away from the joint end is plugged, the hollow area of said shaft is filled with polyethylene, the coverings and the plug are removed and the surface of the polyethylene is covered with apatite in the region of said openings.

17. Method as defined in claim 14, wherein said producing step includes forming said half-tubings with convex outer surfaces, and recesses are formed in the convex outer surfaces of said half-tubings and filled with Porocoat material.

18. Method as defined in claim 14, wherein said producing step includes forming said half-tubings with concave inner surfaces, and recesses are formed in the concave inner surfaces of said half-tubings.

19. Method as defined in claim 14, wherein said half-tubings have a joint end and an end away from said joint end, and an attachment cone is welded onto the joint end of said hollow shaft.

20. Method as defined in claim 14, wherein said half-tubings have a joint end and an end away from said joint end, and an attachment cone is detachably connected to the joint end by means of a bracing ring with a predetermined breaking point.

* * * * *

UNITED STATES PATENT AND TRADEMARK OFFICE
CERTIFICATE OF CORRECTION

PATENT NO. : 5,015,817
DATED : May 14, 1991
INVENTOR(S) : Curt Kranz

It is certified that error appears in the above-identified patent and that said Letters Patent is hereby corrected as shown below:

Claim 6, column 4, line 21, before "convex" and after "formed" insert --in the--.
Claim 11, column 4, line 42, "planned" should read --planed--.
Claim 12, column 4, line 45, "planned" should read --planed--.

Signed and Sealed this

Fourteenth Day of June, 1994

*Attest:*

BRUCE LEHMAN

*Attesting Officer*    Commissioner of Patents and Trademarks